United States Patent
Chen et al.

(10) Patent No.: US 7,228,724 B2
(45) Date of Patent: Jun. 12, 2007

(54) APPARATUS AND PROCESS FOR SENSING TARGET GAS SPECIES IN SEMICONDUCTOR PROCESSING SYSTEMS

(75) Inventors: Philip S. H. Chen, Bethel, CT (US);
Ing-Shin Chen, Danbury, CT (US);
Frank Dimeo, Jr., Danbury, CT (US);
Jeffrey W. Neuner, Bethel, CT (US);
James Welch, New Fairfield, CT (US);
Jeffrey F. Roeder, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 180 days.

(21) Appl. No.: 10/758,825

(22) Filed: Jan. 16, 2004

(65) Prior Publication Data

US 2004/0187557 A1    Sep. 30, 2004

Related U.S. Application Data

(63) Continuation-in-part of application No. 10/273,036, filed on Oct. 17, 2002.

(51) Int. Cl.
*G01N 19/10*    (2006.01)
(52) U.S. Cl. .............. 73/31.05; 73/31.06; 73/204.23
(58) Field of Classification Search .............. 73/31.05, 73/31.06, 23.2, 23.36, 24.06, 23.31, 31.02, 73/204.23; 436/144, 147; 422/83
See application file for complete search history.

(56) References Cited

U.S. PATENT DOCUMENTS 3,270,232 A * 8/1966 Bailey, Jr. et al. ............ 313/38
3,464,269 A * 9/1969 Froger ..................... 73/204.22
3,523,408 A    8/1970 Rosenberg
3,676,293 A    7/1972 Gruber (Continued)

FOREIGN PATENT DOCUMENTS

JP         01-094255 A1    4/1989

(Continued)

OTHER PUBLICATIONS

U.S. Appl. No. 10/273,036, filed Oct. 17, 2002, Frank DiMeo et al.

(Continued)

*Primary Examiner*—Hezron Williams
*Assistant Examiner*—Jacques M. Saint-Surin
(74) *Attorney, Agent, or Firm*—Vincent K. Gustafson; Intellectual Property/Technology Law

(57) ABSTRACT

A gas detector for detecting a fluoro gas species in a gaseous environment containing same, e.g., an effluent from a semiconductor processing tool that employs corrosive fluoro species such as HF, $NF_3$, etc. for etch cleaning. The gas detector preferably employs an elongated nickel-containing gas sensor element that can be vertically mounted on a fluoro-resistant support structure. Since the nickel-containing gas sensor element is sensitive to the fluoro species and is also electrically conductive, it can function both as a sensing component and a heat source when elevated temperature sensing is required. Vertical mounting of such elongated gas sensor element on the support structure significantly improves the signal strength, reduces the response time, minimizes the footprint of the gas detector, and provides structural flexibility for accommodating thermal expansion/contraction of the elongated gas sensor element.

41 Claims, 6 Drawing Sheets

U.S. PATENT DOCUMENTS

| | | | |
|---|---|---|---|
| 3,764,289 A | 10/1973 | Oldham et al. | |
| 3,892,528 A * | 7/1975 | Fredericks | 436/157 |
| 4,480,779 A | 11/1984 | Luc | |
| 4,662,212 A | 5/1987 | Noguchi et al. | |
| 4,723,438 A | 2/1988 | Adler-Golden et al. | |
| 5,072,262 A | 12/1991 | Uekita et al. | |
| 5,104,513 A | 4/1992 | Lee et al. | |
| 5,229,625 A | 7/1993 | Suzuki et al. | |
| 5,356,756 A * | 10/1994 | Cavicchi et al. | 430/315 |
| 5,376,255 A | 12/1994 | Gumbrecht et al. | |
| 5,387,462 A | 2/1995 | Debe | |
| 5,464,966 A | 11/1995 | Gaitan et al. | |
| 5,612,489 A | 3/1997 | Ragsdale et al. | |
| 5,679,576 A * | 10/1997 | Kawai et al. | 436/55 |
| 5,752,410 A | 5/1998 | Bernstein | |
| 5,827,947 A | 10/1998 | Miller et al. | |
| 5,827,952 A | 10/1998 | Mansure et al. | |
| 5,841,017 A | 11/1998 | Baraket et al. | |
| 5,849,113 A * | 12/1998 | Murakami et al. | 148/430 |
| 5,900,128 A | 5/1999 | Gumbrecht et al. | |
| 6,196,052 B1 | 3/2001 | May et al. | |
| 6,202,472 B1 * | 3/2001 | Wezurek et al. | 73/31.05 |
| 6,202,473 B1 | 3/2001 | Stokes et al. | |
| 6,265,222 B1 | 7/2001 | DiMeo, Jr. et al. | |
| 6,321,587 B1 | 11/2001 | Laush | |
| 6,428,713 B1 | 8/2002 | Christenson et al. | |
| 6,463,789 B2 | 10/2002 | Moos et al. | |
| 6,468,642 B1 | 10/2002 | Bray et al. | |
| 6,499,354 B1 | 12/2002 | Najafi et al. | |
| 6,553,335 B2 * | 4/2003 | Huang et al. | 702/184 |
| 6,553,354 B1 | 4/2003 | Hausner et al. | |
| 6,596,236 B2 | 7/2003 | Dimeo, Jr. et al. | |
| 6,634,213 B1 | 10/2003 | O'Connor et al. | |
| 6,637,253 B2 | 10/2003 | Dean et al. | |
| 6,691,554 B2 | 2/2004 | Eastman et al. | |
| 6,694,800 B2 | 2/2004 | Weckstrom et al. | |
| 6,883,371 B2 | 4/2005 | Sugaya et al. | |
| 6,895,805 B2 | 5/2005 | Hoagland | |
| 2001/0009652 A1 | 7/2001 | Amo | |
| 2002/0029613 A1 | 3/2002 | Stetter et al. | |
| 2002/0051132 A1 | 5/2002 | Ohno et al. | |
| 2005/0103097 A1 | 5/2005 | Faltum et al. | |
| 2005/0193800 A1 | 9/2005 | DeBoer et al. | |
| 2005/0230258 A1 | 10/2005 | Dimeo, Jr. et al. | |

FOREIGN PATENT DOCUMENTS

SU            1379632A A1     3/1988

OTHER PUBLICATIONS

Anderson, B., et al., Semiconductor International, Oct. 1993.

Ed P. Hagenmuller, Inorganic Solid Fluorides, Chemistry and Physics, Academic Press, 1985. (See Information Disclosure Statement Box 1).

W. Moritz, et al., Sensors and Actuators B 24-25 (1995) 194-196, "Monitoring of HF and F2 using a field-effect sensor".

Dr. Shigeru Kurosawa, et al., Fluorine in Coatings II, Paper 33, pp. 1-8, "Plasma Polymerisation of Fluorine Contained Polycyclic Compounds: Its Application in Chemical Sensors".

Werner Moritz, et al., The 11th European Conference on Solid State Transucers, Warsaw, Poland, pp. 111-114, Sep. 21-24, 1997, "Gas Sensors for Fluorine Using Different Semiconductor Substrates".

Semiconductor International, "Residual Gas Analysis", Oct. 1997, pp. 94-100.

W. Moritz, et al., "Silicon-Based Sensor for Flourine Gas", American Chemical Society, pp. 119-129.

* cited by examiner

APPARATUS AND PROCESS FOR SENSING TARGET GAS SPECIES IN SEMICONDUCTOR PROCESSING SYSTEMS

CROSS-REFERENCE TO RELATED APPLICATIONS

This is a continuation-in-part of U.S. patent application Ser. No. 10/273,036 filed Oct. 17, 2002 for "APPARATUS AND PROCESS FOR SENSING FLUORO SPECIES IN SEMICONDUCTOR PROCESSING SYSTEMS" in the names of Frank Dimeo Jr., Philip S. H. Chen, Jeffrey W. Neuner, James Welch, Michele Stawasz, Thomas H. Baum, Mackenzie E. King, Ing-Shin Chen, and Jeffrey F. Roeder.

GOVERNMENT RIGHTS IN INVENTION

Work related to the invention hereof was conducted in the performance of NIST ATP Program, Contract Number 70NANB9H3018 for "Integrated MEMS Reactor Gas Monitor Using Novel Thin Film Chemistry for the Closed Loop Process Control and Optimization of Plasma Etch and Clean Reactions in the Manufacturing of Microelectronics." The Government has certain rights in the invention.

BACKGROUND OF THE INVENTION

1. Field of the Invention

The present invention relates generally to a device and a method for sensing a target species, which have utility for monitoring of gaseous compounds and ionic species in semiconductor process operations.

2. Description of the Related Art

In the manufacture of semiconductor devices, the deposition of silicon (Si) and silicon dioxide ($SiO_2$), and subsequent etching, are vital operational steps that currently comprise 8–10 steps or roughly 25% of the total manufacturing process. Each deposition tool and etch tool must undergo a periodic cleaning procedure, sometimes as often as every run, in order to ensure uniform and consistent film properties.

Currently, in etching operations, etch endpoints are reached when a prescribed amount of time has elapsed. Over etch, in which the process gas continues to flow into the reactor chamber after the cleaning etch is finished, is common and leads to longer process cycles, reduced tool lifetimes, and unnecessary global-warming-gas losses to the atmosphere (Anderson, B.; Behnke, J.; Berman, M.; Kobeissi, H.; Huling, B.; Langan, J.; Lynn, S-Y., *Semiconductor International*, October (1993)).

Similar issues are present in the etching of silicon nitride materials when SiN is utilized in semiconductor device structures.

Various analytical techniques, such as FTIR, Optical Emission Spectroscopy, and Ionized Mass Spectroscopy, can be used to monitor the etch process. However, these techniques tend to be expensive, and often require a dedicated operator due to their complexity.

It would therefore be a significant advance in the art to provide a reliable, low-cost gas-sensing capability that will serve to improve the throughput and chemical efficiency of the equipment used for the deposition and etching of silicon-containing materials, including silicon, silicon nitride and silicon dioxide, by reducing and optimizing clean and etch times, and hence reducing chemical usage, lengthening equipment operating life, and decreasing equipment down time.

U.S. patent application Ser. No. 10/273,036 filed Oct. 17, 2002 for "APPARATUS AND PROCESS FOR SENSING FLUORO SPECIES IN SEMICONDUCTOR PROCESSING SYSTEMS" discloses an apparatus and method for sensing solid-state fluoro species, using a fluoro-reactive metal filament weaved around metal packaging posts or Vespel® polyimide blocks on a KF flange. Detection of the fluoro species using such metal filament-based sensors relies on monitoring the resistance changes in the metal filaments caused by their reactions with the fluorine-containing compounds. In order to ensure acceptable sensitivity and signal-to-noise ratio for such metal filament-based sensors, the dimensions and the positions of the metal filaments are controlled and optimized via uses of the metal packaging posts or the Vespel® polyimide blocks, to provide an absolute resistance that is adequate for endpoint detection.

There is a continuing need to discover and develop improved filament-based sensors, by employing new compositions and structures to further enhance the sensitivity, signal-to-noise ratio, and mechanical reliability of such gas sensors, as well as to further reduce the response time and the manufacturing costs thereof.

SUMMARY OF THE INVENTION

The present invention relates generally to apparatus and method for sensing a target gas species, especially a fluoro gas species, in an environment susceptible to the presence of such gas species, such as an ambient environment, a gaseous effluent stream from a semiconductor manufacturing process, etc.

In one aspect, the invention relates to an elongated gas sensor element formed by one or more gas-sensing filaments, such elongated gas sensor element comprising two electrical connection terminals and a longitudinal axis, wherein the longitudinal axis of the sensor element is substantially perpendicular to a line defined by the two electrical connection terminals thereof.

Such elongated gas sensor element may comprise any number of gas-sensing filaments and has any suitable shape or conformation, as long as its longitudinal axis is substantially perpendicular to the line defined by its two electrical connection terminals. In a preferred embodiment of the present invention, the elongated gas sensor element is formed of two gas-sensing filament attached together at first ends thereof and has a wishbone shape.

Such elongated gas sensor element preferably, but not necessarily, comprises a gas-sensitive coating that encapsulates a core structure, wherein the core structure has an electrical resistivity that is higher than that of the gas-sensitive coating and a heat capacity that is lower than that of the gas-sensitive coating. Nickel-containing coating is particularly sensitive to fluoro gas species, and therefore in a particularly preferred embodiment of the present invention, the elongated gas sensor element comprises a nickel-containing coating encapsulating a core structure, such core structure being characterized by a higher electrical resistivity and a lower heat capacity than those of such nickel-containing coating.

Another aspect of the present invention relates to a gas-sensing assembly, which comprises at least one of the above-described elongated gas sensor element mounted on a support structure, wherein such support structure comprises a surface for mounting the two electrical connection terminals of the elongated gas sensor element.

The invention in a further aspect relates to a method for monitoring a fluid locus for the presence of a target gas species therein, said method comprising the steps of:

exposing fluid at said fluid locus to a gas-sensing assembly as described hereinabove;

monitoring at least one property of the elongated gas sensor element of such gas-sensing assembly; and responsively generating an output signal when the elongated gas sensor element exhibits a change in the at least one property thereof, indicating the presence of the target gas species in the fluid locus, or a change in concentration of the target gas species in the fluid locus.

A still further aspect of the present invention relates to a method for fabricating an elongated gas sensor element having a wishbone shape, comprising the steps of:

(a) aligning a pair of gas-sensing filaments side by side; and (b) connecting such pair of gas-sensing filaments at first ends thereof, while leaving the opposite, second ends of said pair of gas-sensing filaments separated from each other, wherein the separated opposite, second ends of such pair of gas-sensing filaments form the two electrical connection terminals of the wishbone-shaped gas sensor element.

Alternatively, such wishbone-shaped gas sensor element can be formed by a method comprising the steps of:

(a) aligning a pair of filaments side by side;

(b) connecting such pair of filaments at first ends thereof, while leaving the opposite, second end of such pair of filaments separated from each other, so as to form a wishbone-shaped precursor structure; and (c) forming a gas-sensitive coating over such wishbone-shaped precursor structure.

Yet another aspect of the present invention relates to a gas-sensing assembly arranged in sensing relationship to a process chamber that is susceptible to presence of one or more target fluoro gas species, wherein such gas-sensing assembly comprises a nickel-containing gas sensor element mounted on a surface of a support structure and coupled to means for detecting a change in at least one property of such gas sensor element upon contact with the target fluoro gas species and responsively generating an output signal indicative of the presence of the target fluoro gas species, wherein such nickel-containing gas sensor element has a longitudinal axis that is oriented perpendicular to or substantially perpendicular to the mounting surface of the support structure.

As used herein, the term "fluoro species" is intended to be broadly construed to encompass all fluorine-containing materials, including without limitation, gaseous fluorine compounds, fluorine per se in atomic and diatomic ($F_2$) forms, fluorine ions, and fluorine-containing ionic species. The fluoro species may for example include species such as $NF_3$, $SiF_4$, $C_2F_6$, HF, $F_2$, $COF_2$, $ClF_3$, $IF_3$, $XeF_2$ etc., and activated fluorine-containing species (denoted collectively as F°) thereof, including ionized fragments, plasma forms, etc.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The contents of U.S. patent application Ser. No. 10/273, 036 filed Oct. 17, 2002 for "APPARATUS AND PROCESS FOR SENSING FLUORO SPECIES IN SEMICONDUCTOR PROCESSING SYSTEMS" and U.S. Pat. No. 6,265, 222 issued Jul. 24, 2001 for "MICRO-MACHINED THIN FILM HYDROGEN GAS SENSOR, AND METHOD OF MAKING AND USING THE SAME" are incorporated herein by reference in their entirety for all purposes.

While the invention is described more fully hereinafter with specific reference to applications in semiconductor process control, it is to be appreciated that the utility of the invention is not thus limited, but rather extends to a wide variety of other uses and applications, including, without limitation, deployment in life safety systems, room or ambient environment monitoring operations, and other industrial as well as consumer market gas-sensing applications.

The present invention provides a new filament-based gas sensor element, which is elongated in shape and has two electrical connection terminals and a longitudinal axis. The two electrical connection terminals of such gas sensor element define a line, to which the longitudinal axis of the gas sensor element is substantially perpendicular.

For a filament-based gas sensor of given composition, the aspect ratio between its longitudinal dimension (L) and its lateral dimension (D) has significant influences on its signal strength and response time. Generally speaking, the larger the L/D ratio, the higher the signal strength and the shorter the response time.

Since the longitudinal axis of the new gas sensor element of the present invention is substantially perpendicular to the lateral line defined by the two electrical connection terminals, the longitudinal dimension of such gas sensor element (i.e., the dimension along its longitudinal axis) is not limited by the lateral distance between its electrical connection terminals, and it therefore can be increased to maximize the L/D ratio, which in turn improves signal strength and reduces response time.

Figure 1:
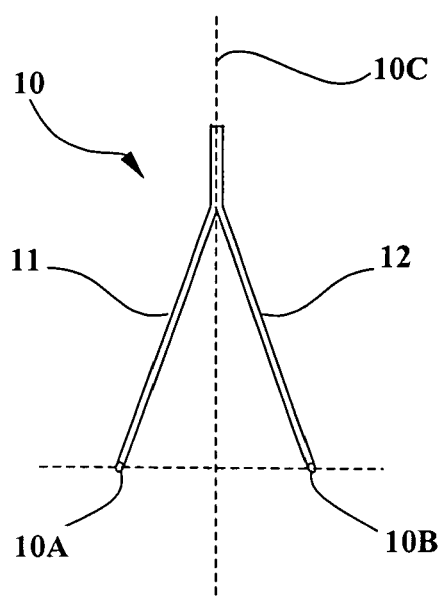
FIG. 1 shows a wishbone-shaped gas sensor element formed by two gas-sensing filaments, according to one embodiment of the present invention.

For illustration purposes, FIG. 1 shows an elongated gas sensor element 10, according to a preferred embodiment of the present invention. The elongated gas sensor element 10 has a wishbone-shape and is formed by attaching two gas-sensing filaments 11 and 12 together at their upper ends, while leaving the lower ends of such filaments separated from each other. The separated lower ends of the filaments 11 and 12 therefore form two electrical connection terminals 10A and 10B, by which an electrical current can be passed through the elongated gas sensor element 10 for gas-sensing at elevated temperatures. The longitudinal axis 10C of the gas sensor element 10 (as shown by the vertical dotted line) is oriented perpendicular to the line (as shown by the horizontal dotted line) defined by the two electrical connection terminals 10A and 10B.

In such manner, the elongated gas sensor element 10 has a longitudinal dimension that is not limited by the distance between the two electrical connection terminals. As a result, the longitudinal dimension of such elongated gas sensor element 10 can be increased significantly for improving signal strength and reducing response time required for gas-sensing, without having to increase the lateral dimension thereof (i.e., either the dimension along the line defined by the two electrical connection terminals or the distance between the two electrical connection terminals).

Figure 2:
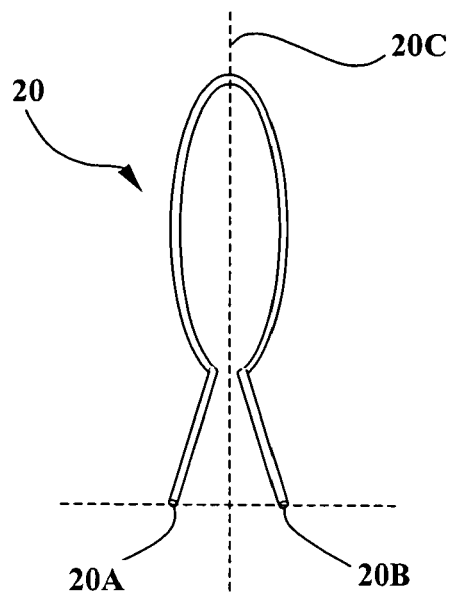
FIGS. 2–4 show elongated gas sensor elements of various shapes and configurations.

FIG. 2 shows another elongated gas sensor element 20, according to an alternative embodiment of the present invention. The elongated gas sensor element 20 has a keyhole-shape and is formed by bending and shaping a single gas-sensing filament. The two ends of such bent/shaped gas-sensing filament form the two electrical connection terminals 20A and 20B of the gas sensor element 20, and an electrical current therefore can be passed through the elongated gas sensor element 20 via such electrical connection terminals 20A and 20B for gas-sensing at elevated temperatures. The longitudinal axis 20C of the gas sensor element 20 (as shown by the vertical dotted line) is oriented perpendicular to the line (as shown by the horizontal dotted line) defined by the two electrical connection terminals 20A and 20B.

Figure 3:
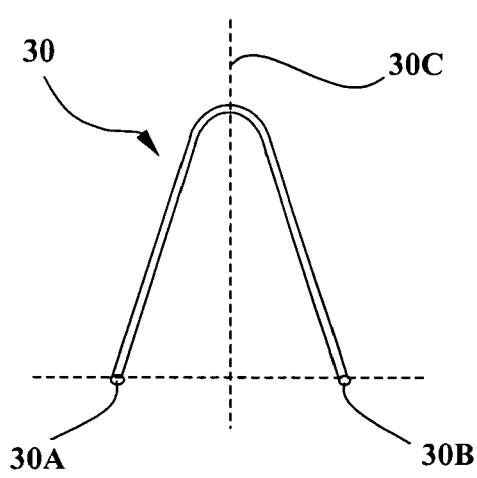

FIG. 3 shows another elongated gas sensor element 30, which has an open hairpin-shape and is formed by bending a single gas-sensing filament. The two ends of the bent gas-sensing filament form the two electrical connection terminals 30A and 30B of the gas sensor element 30, and an electrical current therefore can be passed through the elongated gas sensor element 30 via such electrical connection terminals 30A and 30B for gas-sensing at elevated temperatures. The longitudinal axis 30C of the gas sensor element 30 (as shown by the vertical dotted line) is oriented perpendicular to the line (as shown by the horizontal dotted line) defined by the two electrical connection terminals 30A and 30B.

Figure 4:
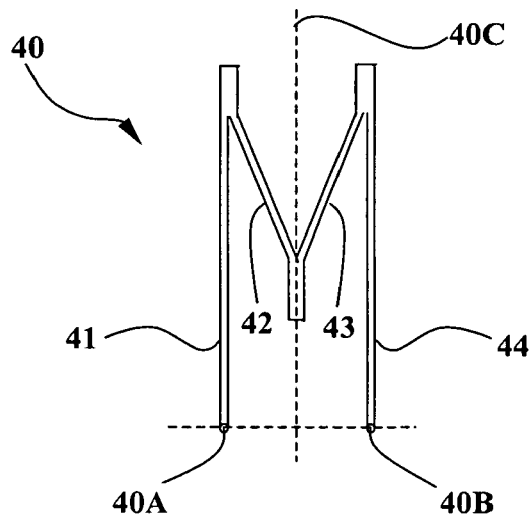

FIG. 4 shows another elongated gas sensor element 40, which has an M-shape and is formed by attaching four gas-sensing filaments 41, 42, 43, and 44 in a zigzagged manner at respective ends. One end of filament 41 and one end of filament 44 form the two electrical connection terminals 40A and 40B for the gas sensor element 40, and an electrical current therefore can be passed through the elongated gas sensor element 40 via such electrical connection terminals 40A and 40B for gas-sensing at elevated temperatures. The longitudinal axis 40C of the gas sensor element 40 (as shown by the vertical dotted line) is oriented perpendicular to the line (as shown by the horizontal dotted line) defined by the two electrical connection terminals 40A and 40B.

Note that many other shapes and configurations of the elongated gas sensor element are available and can be employed for practice of the present invention, but for illustration purposes, only a few exemplary embodiments are shown in FIGS. 1–4 herein. A person ordinarily skilled in the art can readily modify the shapes and configurations of the elongated gas sensor elements as shown in FIGS. 1–4, consistent with the disclosure provided herein and without undue experimentation, and any such modifications are within the broad scope of the present invention.

To achieve high gas sensitivity and minimum response delay, the L/D ratio of the elongated gas sensor element of the present invention is preferably larger than 3, and more preferably larger than 10, and most preferably larger than 50.

The elongated gas sensor element as described hereinabove can be mounted on a support structure, to form a gas-sensing assembly that can be placed at a fluid locus for detecting the presence of a target gas species. Such gas-sensing assembly may also comprise means for detecting changes in such gas sensor element upon contact thereof with the target gas species, and means for responsively generating an output signal indicative of such changes.

In a preferred embodiment, the support structure comprises a fluoro-resistant flange material, e.g., a KF flange formed of Vespel® polyimide or aluminum. Vespel® polyimide is a preferred polyimide material of construction in various embodiments of the invention, but it will be recognized that other polyimide or polymeric (e.g., polysulfone) materials of construction may alternatively be used.

Such support structure provides physical support as well as electrical connection to the gas sensor element via the two electrical connection terminals, and the supporting or mounting surface of the support structure therefore must be able to accommodate at least the two electrical connection terminals of the gas sensor element. In order to minimize the surface area or footprint of the support structure, the gas sensor element of the present invention is arranged and configured so that its longitudinal axis is substantially perpendicular to the supporting or mounting surface of the support structure. In such manner, the footprint of the support structure is reduced without affecting or comprising the L/D ratio of the gas sensor element.

Figure 5:
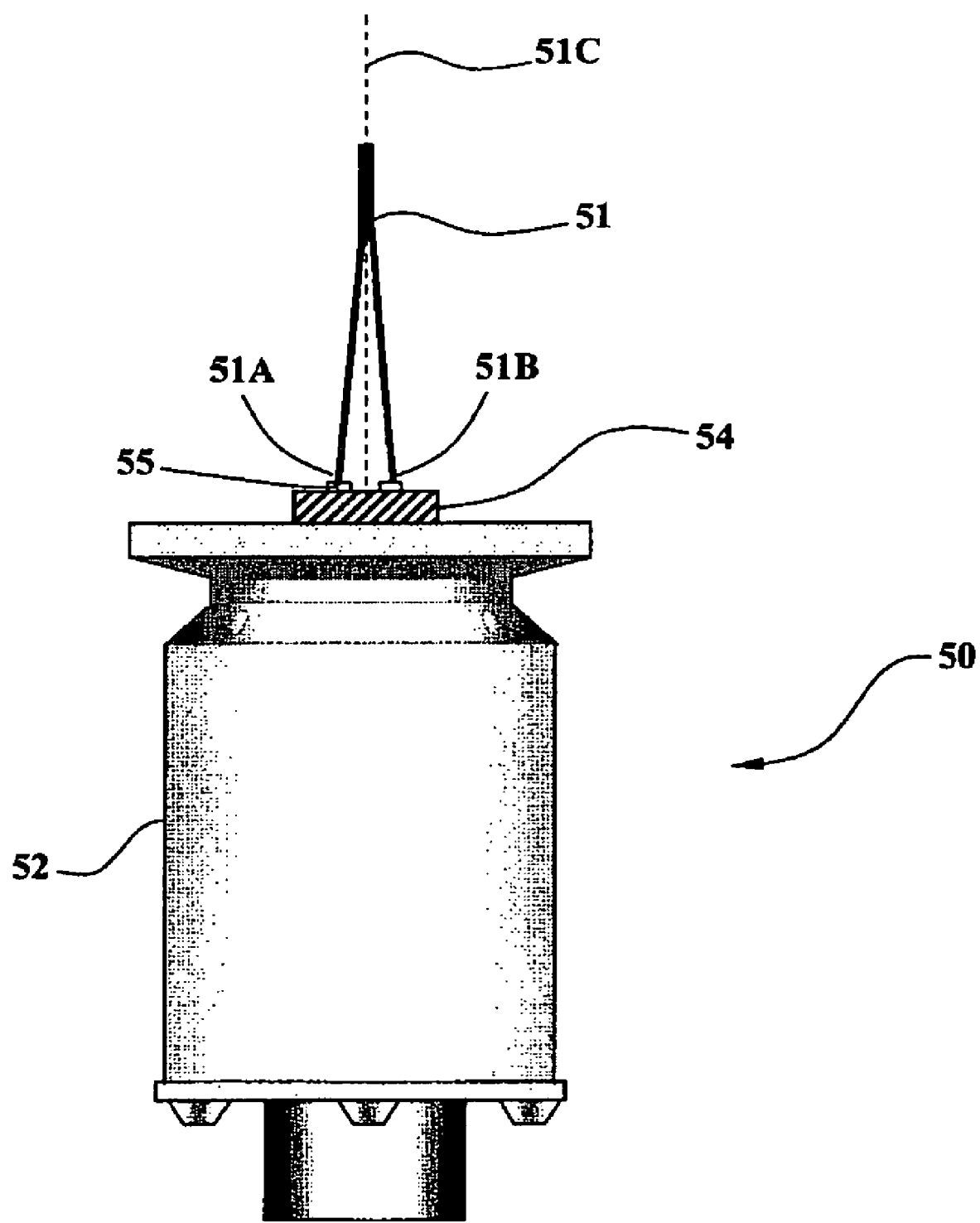
FIG. 5 shows a wishbone-shaped gas sensor element that is vertically mounted on a support structure, according to one embodiment of the present invention.

FIG. 5 shows a gas-sensing assembly 50 comprising a support structure 52 with a planar supporting or mounting surface 54. The mounting surface 54 comprises two press-fit pins 55 for mounting the two electrical connection terminals 51A and 51B of the wishbone-shaped gas sensor element 51. In such manner, the gas sensor element 51 is mounted to the support structure 52 in a "vertical" manner, i.e., having its longitudinal axis 51C oriented perpendicular to or substantially perpendicular to the mounting surface 54 of the support structure 52.

Because the longitudinal axis of the gas sensor element is substantially perpendicular to the mounting surface of the support structure, the longitudinal dimension of the gas sensor element can be increased significantly for improving signal strength and reducing response time, but without having to increase the area of the mounting surface. Therefore, the gas-sensing assembly of the present invention advantageously provides enhanced gas-sensing capacity with reduced footprint.

Further, vertical mounting of the gas sensor element provides flexibility to accommodate thermal expansion and contraction of such gas sensor element along its longitudinal axis.

Therefore, the present invention achieves significant advancement in the gas-sensing field, by providing an elongated gas sensor element as described hereinabove, which can be vertically mounted on a support structure.

As is well known, fluoro species react with most metals to form compounds that have a high, and sometimes, mixed oxidation state (Inorganic Solid Fluorides, Chemistry and Physics. Academic Press, 1985, Ed P. Hagenmuller). Many of the transition metals and noble metals (including, for example, but not limited to Ni, Cu, Al, Ti, V, Cr, Mn, Nb, Mo, Ru, Pd, Ag, Ir, and Pt) readily form various non-volatile fluorinated compounds in contact with such fluoro species.

The present invention therefore employs fluoro-reactive metal filaments to form the elongated gas sensor element as described hereinabove. By monitoring changes in the properties of such metal filaments as caused by their reaction with fluoro species, one can determine the presence and/or concentration of one or more target fluoro species in a particular gaseous environment, such as a effluent gas stream discharged by a semiconductor chamber clean process.

Specifically, the electrical resistance increase observed for a fluoro-reactive metal filament, when placed in a gaseous environment susceptible to contamination by a fluoro species, has been found to be a good indicator of the presence and concentration of such fluoro species in the environment. Because the metal filament possesses higher thermal conductivity than the gaseous environment, a significant portion of the heat generated by the exothermic reactions between the metal filament and the fluoro species is channeled to the metal filament, causing temperature increase in such metal filament, which in turn raises the electrical resistance of such metal filament through additional phonon scattering.

A figure-of-merit (FOM) for various gas sensors can be define on the basis of a "slew rate" (SR), which is the ratio of signal strength over response time. Among pure metals that are fluorine-resistant, nickel is found to possess the highest FOM (11.1 $n\Omega \cdot cm^2/J$, in comparison with 4.66 $n\Omega \cdot cm^2/J$ measured for aluminum and 1.97 $n\Omega \cdot cm^2/J$ measures for copper). Monel, a nickel-copper alloy, is characterized by a FOM (21.2 $n\Omega \cdot cm^2/J$) that is even higher than that of nickel.

Therefore, an important aspect of the present invention relates to the uses of nickel-containing filaments, which contains either pure nickel or nickel alloys, in gas-sensing assembly for detection of target fluoro species.

One preferred embodiment of the invention employs a gas-sensing filament comprising a fluoro-reactive coating structure that contains nickel or nickel alloy, while such coating structure encapsulates a high resistivity, low thermal mass core structure, which is characterized by an electrical resistivity that is higher than that of the coating structure and a heat capacity (i.e., the product of specific heat $C_p$ and density D) that is lower than that of the coating structure.

Preferably, such core structure is characterized by an electrical resistivity that is at least fifty (50) times larger than that of the coating structure, and a heat capacity that is less than three fourth (¾) of that of the coating structure. More preferably, such core structure is characterized by an electrical resistivity that is at least one thousand (1000) times larger than that of the coating structure, and a heat capacity that is less than one half (½) of that of the coating structure. Most preferably, such core structure is characterized by an electrical resistivity that is at least 10 $m\Omega \cdot cm$ and a heat capacity that is less than 2.5 $J/K \cdot cm^3$.

Many combinations of materials are available for forming such coating and core structures. Without limiting the broad scope of the present invention, examples of materials suitable for forming the coating and core structures are herein provided, which include: (1) pure nickel for the coating and a nickel alloy (such as Monel) for the core; (2) pure nickel or nickel alloy for the coating and silicon carbide for the core; (3) pure nickel or nickel alloy for the coating and carbon for the core, etc.

Silicon carbide is particularly preferred for forming the core structure in the present invention, because the high electrical resistivity (usually greater than 10 $m\Omega \cdot cm$) and low heat capacity (usually less than 2.5 $J/K \cdot cm^3$) of silicon carbide further enhances the signal strength and responsiveness of the nickel-containing filament sensor, without inducing significant heat loss. Moreover, silicon carbide is resistant to attack by the corrosive fluorine plasma, which, although not a necessary feature of the encapsulated core structure, advantageously improves the mechanical robustness and reliability of the filament sensor when used in corrosive gaseous environment for detecting fluoro species.

Figure 6:
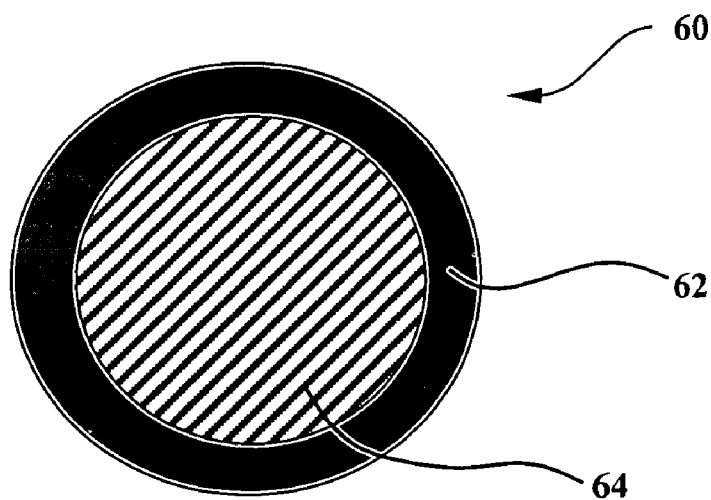
FIG. 6 illustratively depicts the cross-sectional view of a gas-sensing filament that comprises a Monel coating structure encapsulating a silicon carbide core structure, according to one embodiment of the present invention.

FIG. 6 illustratively shows the cross-sectional view of a gas-sensing filament 60 according to one embodiment of the invention, which comprises a core structure 64 made of β-silicon carbide encapsulated by a coating 64 fabricated by using the nickel-copper alloy, Monel.

Composite structures comprising multiple layers of high resistivity, low thermal mass materials can also be used to form the core structure for the filament sensors of the present invention. Various combinations and configurations of suitable core materials can be employed to further improve the figure of merit (FOM) of the filament sensors. In one instance, the SCS silicon carbide fibers manufactured by Specialty Materials at Lowell, Mass. are used as the core structure, upon which a thin layer of nickel is formed as the gas-sensing layer.

Figure 7:
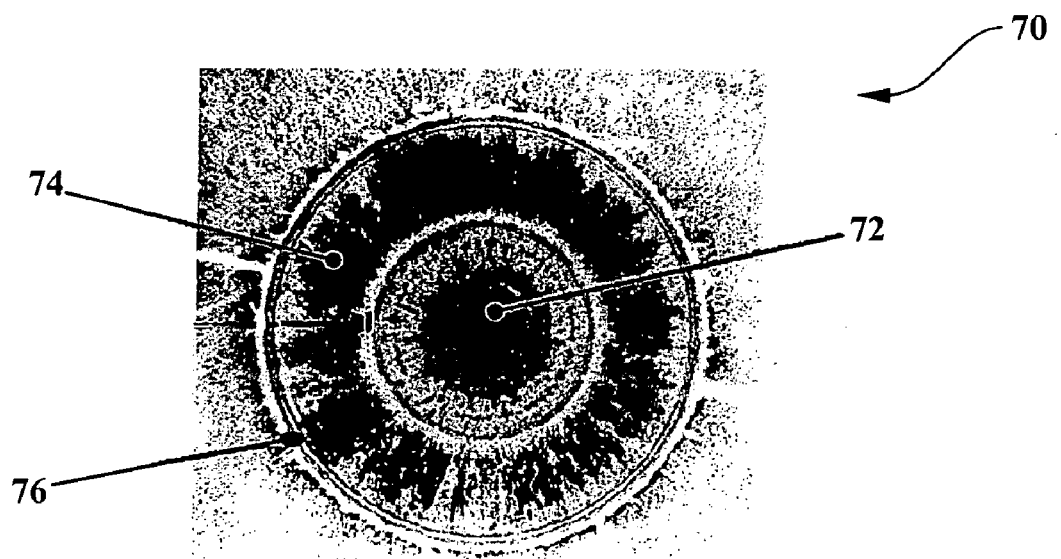
FIG. 7 shows a partial cross-section view of a composite core fiber that is suitable for forming a gas-sensing filament according to one embodiment of the present invention.

FIG. 7 shows a partial cross-sectional view of a composite SCS silicon carbide fiber 70 having an overall diameter of from about 78 microns to about 140 microns, which includes a carbon core 72 enclosed in a β-SiC sheath 74 with a carbon rich surface 76. The SCS silicon carbide fibers have a heat capacity ($C_p$ times D) that is about one half of that of nickel, and are resistant to fluoro species.

For forming a wishbone-shaped gas sensor element, a pair of nickel-coated SiC carbon fibers can be aligned side by side and then attached at one ends thereof, while leaving the opposite ends of such nickel-coated SiC carbon fibers unattached and separated from each other, which form the two electrical connection terminals for the gas sensor element.

Alternatively, such wishbone-shaped gas sensor element may be formed by aligning a pair of uncoated SiC carbon fibers and attaching them at one end thereof, so as to form a wishbone-shaped precursor structure, which can be subsequently coated with a layer of gas-sensitive material, such as nickel or nickel alloy.

For quantitatively determining the signal strength and responsiveness of the gas sensor element of the present invention, effluent gas containing fluoro species from a semiconductor cleaning chamber was concurrently contact with a first gas-sensing assembly comprising a vertically mounted wishbone-shaped gas sensor element (WISHBONE) and a second gas-sensing assembly comprising a horizontally mounted straight nickel-coated SiC carbon fiber (XENA), both of which generated a set of sensor signal outputs. The signal outputs produced by the vertically mounted wishbone-shaped gas sensor element of the invention and by the horizontally mounted straight nickel-coated SiC carbon fiber were then superposed as a function of time, to visualize the relative signal strength and responsiveness thereof.

Figure 8:
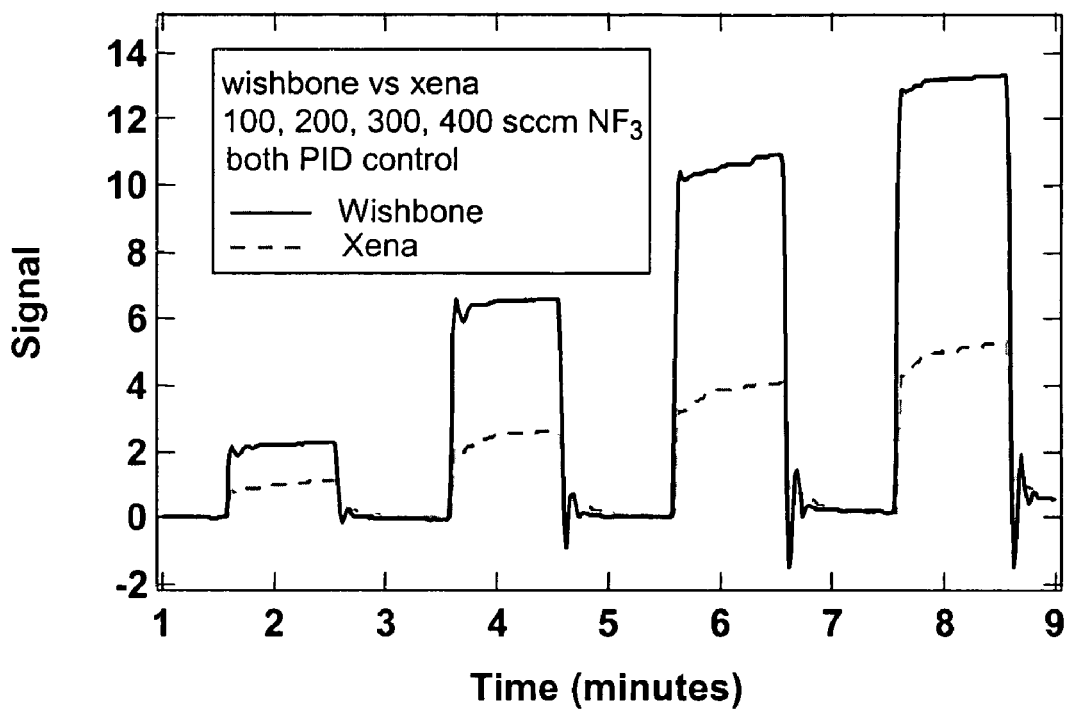
FIG. 8 shows the signal responses produced over time by a vertically mounted wishbone-shaped gas-sensing element (WISHBONE), in comparison with the signal responses produced over time by a horizontally mounted straight nickel-coated SiC carbon fiber (XENA) under the same testing conditions.

FIG. 8 shows in the solid line the signal outputs generated over time by the gas-sensing assembly comprising the vertically mounted wishbone-shaped gas sensor element, which was formed by two nickel-coated SiC carbon fibers. The signal outputs generated over time by the gas-sensing assembly comprising the horizontally mounted straight nickel-coated SiC carbon fiber is shown thereby in dotted lines. It is clear that the wishbone-shaped gas sensor element provides a faster response and much stronger signals in comparison with those provided by the straight nickel-coated SiC carbon fiber sensor.

The gas-sensing filaments or the nickel-containing filaments of the present invention are preferably characterized by average outer diameters of less than 500 microns, more preferably less than 150 microns or less than 50 microns, and most preferably in a range of from about 0.1 micron to about 30 microns, and average lengths of more than 1 cm, more preferably more than 10 cm, and most preferably more than 20 cm.

The present invention provides a solution to such problem, by first fabricating a gas-sensing assembly using one or more gas-sensing filaments, or preferably nickel-containing filaments, that has an average diameter larger than 50 microns, and then electrochemically thinning such gas-sensing filament to reduce its average diameter less than 50 microns. In this event, the thinning process is carried out on a gas-sensing filament that has already been incorporated into the gas-sensing assembly, and no further handling of the gas-sensing filament is necessary after thinning, therefore significantly reducing the risk of damaging the ultra-thin filament.

Figure 9:
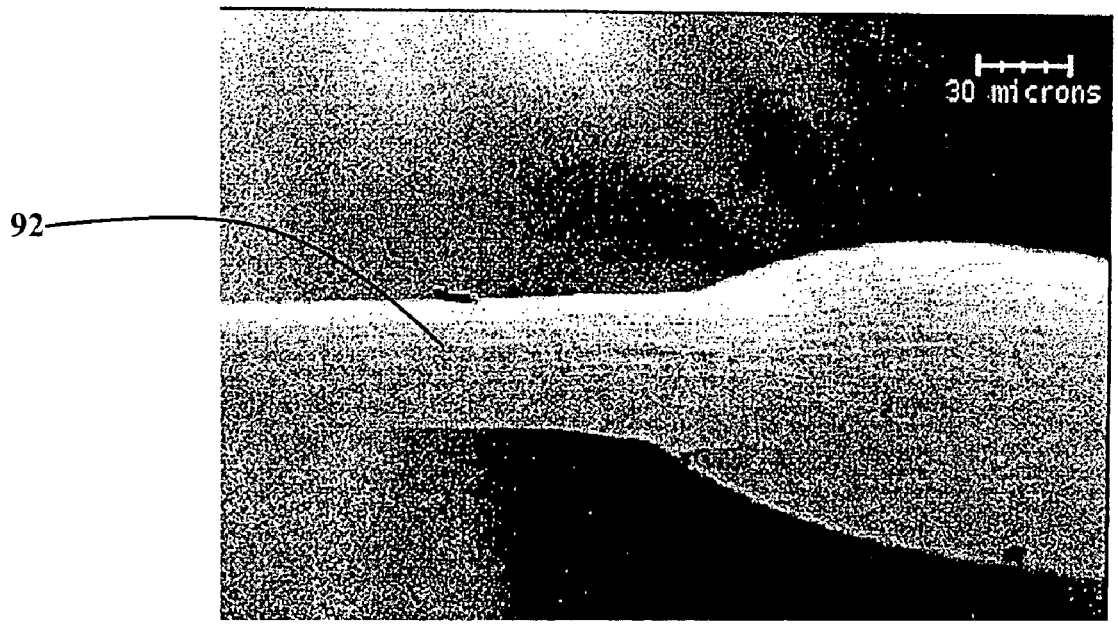
FIG. 9 shows a perspective view of a nickel filament comprising a neck portion that is electrochemically thinned, according to one embodiment of the present invention.

FIG. 9 shows a partially thinned nickel filament 92, which has an original average diameter of about 100–110 microns. After electrochemical thinning at a portion of such filament 92, the average diameter is effectively reduced to about 35–45 microns.

Improved sensitivity can also be achieved by forming a nickel-containing filament having a porous surface, which functions to increase the surface area $A_s$ of the filament sensor without comprising the cross-sectional area $A_c$ thereof.

Figure 10:
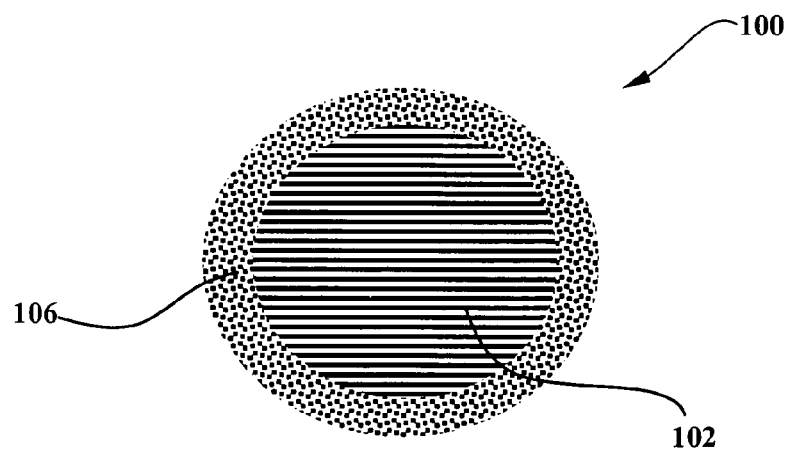
FIG. 10 illustratively depicts the cross-sectional view of a gas-sensing filament comprising a porous nickel coating, according to one embodiment of the present invention.
Figure 11:
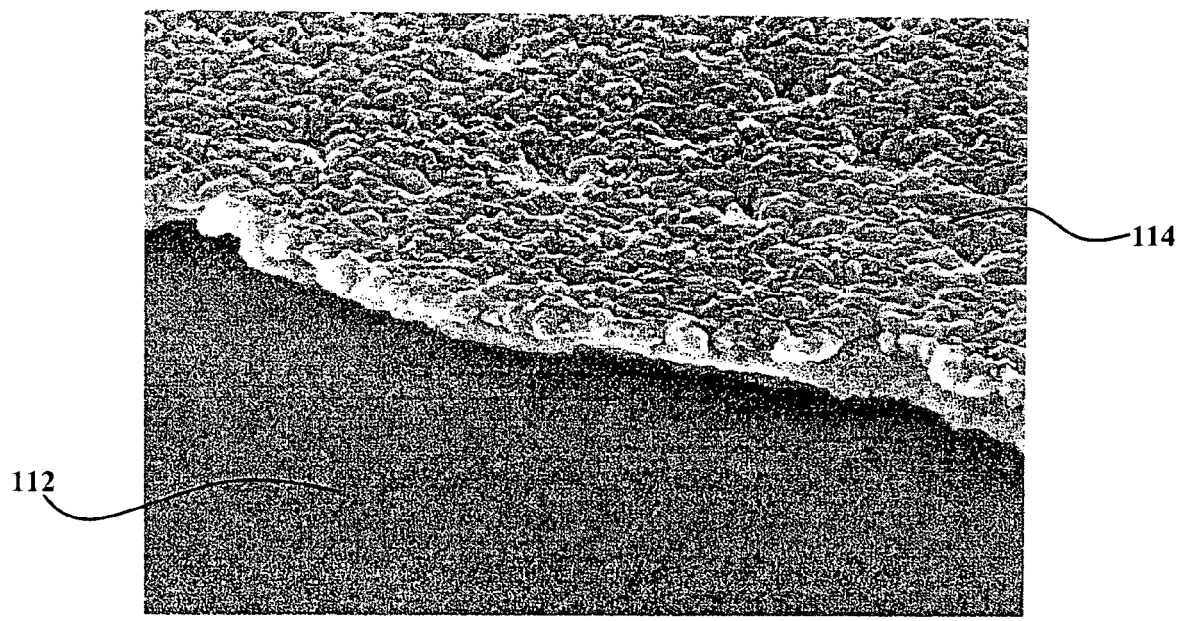
FIG. 11 is a SEM micrograph of a gas-sensing filament comprising a porous nickel coating formed on a dense substrate, according to one embodiment of the present invention.

FIG. 10 illustratively shows a nickel-containing filament 100 that comprises a relatively dense core 102 and a porous surface 106. The porous surface of the nickel-containing filament may be provided by a two-stage plating process, wherein at an initial seeding stage, the plating of nickel or nickel alloy on a substrate (such as a core structure) is carried out at a relatively low speed, so as to allow improved bonding between the layer of nickel or nickel alloy plated and the underlying substrate, and wherein at the subsequent growth stage, the plating is conducted at a significantly faster rate, so as to form rough plating surface with microporosity or nanoporosity. FIG. 11 shows a SEM micrograph of a nickel coating 114 of nanoporosity formed on a non-porous, dense substrate 112.

Figure 12:
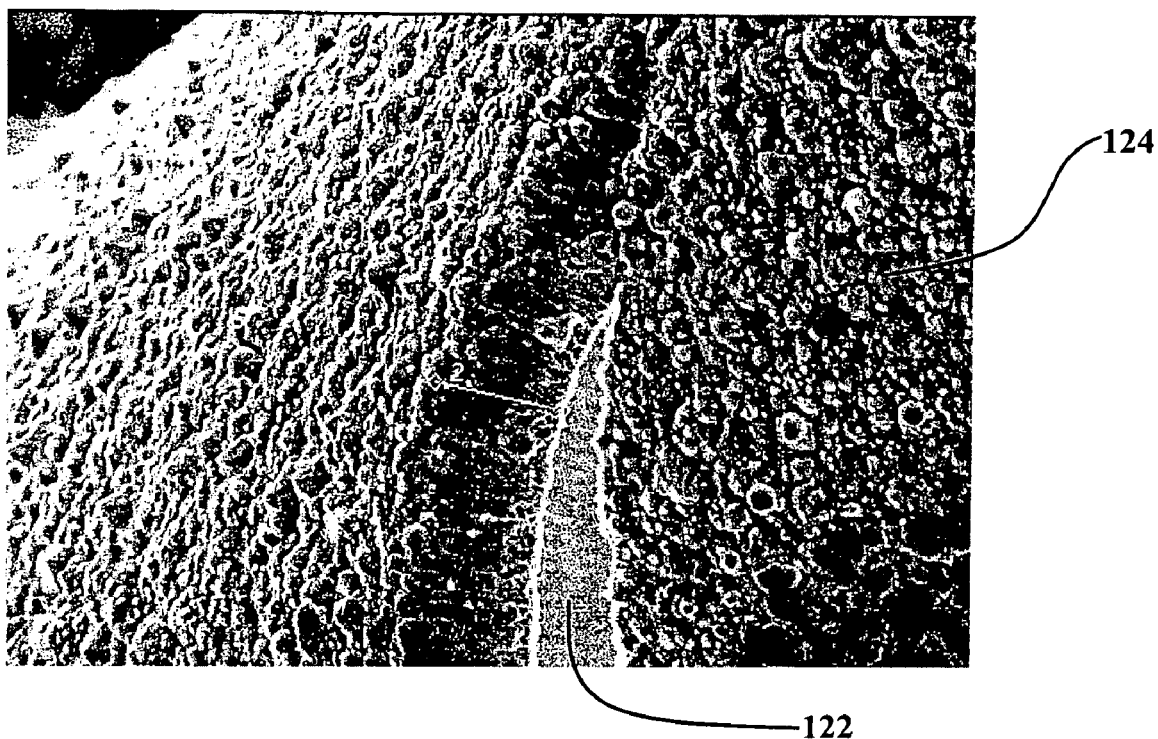
FIG. 12 is a SEM micrograph of a gas-sensing filament comprising a porous nickel coating characterized by an open pore structure, according to one embodiment of the present invention.

Alternatively, porous nickel coating can be formed by using liquid crystal templates from proper surfactants. This technique is particularly suitable for forming open pore structures, which maximizes the fluoro-accessible surface area of the porous nickel coating and therefore further improves the sensitivity of the filament sensor. FIG. 12 shows a SEM micrograph of a porous nickel coating 124 characterized by open pore structures and having a thickness of about 4.93 microns, formed on a dense silicon carbide substrate 122.

The performance of the gas-sensing filaments or nickel-containing filaments of the present invention can be further enhanced, by using various nickel-copper alloys, such as Monel, which are characterized by electrical resistance and figure of merit (FOM) that are even higher than the pure nickel. Such nickel-copper alloy may further comprise other fluorine-resistant metals such as Al, Ti, V, Cr, Mn, Nb, Mo, Ru, Pd, Ag, Ir, and Pt. In a particularly preferred embodiment of the present invention, a nickel-copper-aluminum alloy is used to form the gas-sensing filament.

The present invention thus provides a group of novel filament-based gas sensors that can be coupled in sensing relationship to a process chamber, e.g., a semiconductor process chamber, and can achieve various degrees of sensitivity and responsiveness, by appropriate selection of materials and structures for such filament sensors.

The gas sensor assembly of the invention may include a single gas sensor as described hereinabove, or a plurality of such gas sensors, wherein the multiple gas sensor elements provide redundancy or back-up sensing capability, or in which different ones of the multiple sensor elements are arranged for sensing of different fluoro species in the stream or gas volume being monitored, or in which different ones of the sensor elements in the array are operated in different modes, or in interrelated modes, such as for production of respective signals that are algorithmically manipulated, e.g., subtractively, to generate a net indicating signal, or alternatively, additively to produce a composite indicating signal, or in any other suitable manner in which the multiplicity of sensor elements is efficaciously employed to monitor the flow of species in the stream or fluid volume of interest, for generation of correlative signal(s) for monitoring or control purposes. Alternatively, or additionally, different ones of the multiple sensor elements may be operated in different operating modes, e.g., resistively, conductively, pulsed, a DC mode, an AC mode, etc.

In connection with the use of arrays of gas-sensing elements, advanced data processing techniques can be used to enhance the output of the sensor system. Examples of such techniques include, but are not limited to, the use of compensating signals, the use of time-varying signals, heater currents, lock-in amplifying techniques, signal averaging, signal time derivatives, and impedance spectroscopy techniques. In addition, advanced techniques that fall into the category of chemometrics may also be applied. These techniques include least squares fitting, inverse least squares, principal component regression, and partial least square data analysis methods.

The gas-sensing element(s) of the invention may therefore be coupled in a suitable manner, within the skill of the art, to transducers, computational modules, or other signal processing units, to provide an output indicative of the present or change in amount of one or more fluoro species in the fluid environment being monitored.

It will be recognized that micro-hotplate structures of a type adaptable to the practice of the present invention may be employed in the gas sensor assemblies of the present invention, as more fully described in U.S. Pat. No. 6,265,222 issued Jul. 24, 2001 in the names of Frank DiMeo, Jr. and Gautam Bahndari, the disclosure of which hereby is incorporated herein by reference in its entirety.

Although the invention has been variously described herein with reference to illustrative embodiments and features, it will be appreciated that the embodiments and features described hereinabove are not intended to limit the invention, and that other variations, modifications and other embodiments will readily suggest themselves to those of ordinary skill in the art, based on the disclosure herein. The invention therefore is to be broadly construed, consistent with the claims hereafter set forth.

What is claimed is:

1. An elongated gas sensor element formed by one or more gas-sensing filaments, said elongated gas sensor element comprising two electrical connection terminals and having a longitudinal axis, wherein the longitudinal axis of the sensor element is substantially perpendicular to a line defined by the two electrical connection terminals thereof, wherein said one or more gas-sensing filament are interactive with at least one predetermined target gas species to produce a signal indicative of any of presence and concentration of the at least one gas species.

2. The elongated gas sensor element of claim 1, wherein said one or more gas-sensing filaments are characterized by an average diameter of less than about 500 microns.

3. The elongated gas sensor element of claim 1, wherein said one or more gas-sensing filaments are characterized by an average diameter of less than about 150 microns.

4. The elongated gas sensor element of claim 1, wherein said one or more gas-sensing filaments are characterized by an average diameter of less than about 50 microns.

5. The elongated gas sensor element of claim 1, wherein said one or more gas-sensing filaments are characterized by an average diameter in a range of from about 0.1 micron to about 30 microns.

6. The elongated gas sensor element of claim 1, characterized by a length of more than about 1 cm along its longitudinal axis.

7. The elongated gas sensor element of claim 1, characterized by a length of more than about 10 cm along its longitudinal axis.

8. The elongated gas sensor element of claim 1, characterized by a length of more than 20 cm along its longitudinal axis.

9. The elongated gas sensor element of claim 1, characterized by a wishbone shape.

10. The elongated gas sensor element of claim 1, comprising a nickel-containing coating that encapsulates a core structure, wherein said core structure has an electrical resistivity that is higher than that of the nickel-containing coating and a heat capacity that is lower than that of the nickel-containing coating.

11. The elongated gas sensor element of claim 10, wherein the electrical resistivity of the core structure is at least about fifty times higher than that of the nickel-containing coating, and wherein the heat capacity of said core structure is less than three-fourths of that of the nickel-containing coating.

12. The elongated gas sensor element of claim 10, wherein the electrical resistivity of the core structure is at least about a thousand times higher than that of the nickel-containing coating, and wherein the heat capacity of said core structure is less than one-half of that of the nickel-containing coating.

13. The elongated gas sensor element of claim 10, wherein the electrical resistivity of the core structure is at least about 10 mΩ·cm, and wherein the heat capacity of said core structure is less than 2.5 J/K·cm$^3$.

14. The elongated gas sensor element of claim 10, wherein said core structure comprises a nickel-copper alloy, and wherein said nickel-containing coating consists essentially of nickel.

15. The elongated gas sensor element of claim 10, wherein said core structure comprises silicon carbide.

16. The elongated gas sensor element of claim 10, wherein said core structure comprises a composite fiber having multiple layers of different materials.

17. The elongated gas sensor element of claim 10, wherein said core structure comprises a composite fiber having a carbon core fiber coated with a silicon carbide layer.

18. A method for fabricating the elongated gas sensor element of claim 9, comprising the steps of:
  (a) aligning a pair of gas-sensing filaments side by side; and
  (b) connecting said pair of gas-sensing filaments at first ends thereof, while leaving the opposite, second ends of said pair of gas-sensing filaments separated from each other, wherein the separated opposite, second ends of said pair of gas-sensing filaments form the two electrical connection terminals of the elongated gas sensor element.

19. The method of claim 18, wherein each of said gas-sensing filaments is formed by coating a filament with a gas-sensitive material.

20. A method for fabricating the elongated gas sensor element of claim 9, comprising the steps of:
  (a) aligning a pair of filaments side by side;
  (b) connecting said pair of filaments at first ends thereof, while leaving the opposite, second end of said pair of filaments separated from each other, so as to form a wishbone-shaped precursor structure; and
  (c) forming a gas-sensitive coating over said wishbone-shaped precursor structure.

21. The elongated gas sensor element of claim 1, wherein said one or more gas-sensing filaments comprise a nickel-copper alloy.

22. The elongated gas sensor element of claim 1, wherein said one or more gas-sensing filament comprise a nickel-copper-aluminum alloy.

23. The elongated gas sensor element of claim 22, wherein said one or more gas-sensing filament further comprise one or more metals selected from the group consisting of Ti, V, Cr, Mn, Nb, Mo, Ru, Pd, Ag, Ir, and Pt.

24. The elongated gas sensor element of claim 1, wherein said one or more gas-sensing filament comprise a porous coating of nickel or nickel alloy.

25. The elongated gas sensor element of claim 24, wherein said porous coating is characterized by open pore structures.

26. A gas-sensing assembly comprising the elongated gas sensor element of claim 1 mounted on a support structure, wherein said support structure comprises a surface for mounting the two electrical connection terminals of the elongated gas sensor element.

27. The gas-sensing assembly of claim 26, further comprising a detector adapted to detect a change in at least one property of said elongated gas sensor element upon contact with a target gas species, and a signal generator adapted to generate an output signal indicative of presence of said target gas species.

28. The gas-sensing assembly of claim 27, wherein the target gas species comprises a fluoro species selected from the group consisting of $NF_3$, $SiF_4$, $C_2F_6$, HF, $F_2$, $COF_2$, $ClF_3$, $IF_3$, and activated species thereof.

29. The gas-sensing assembly of claim 28, wherein the support structure comprises a material that is resistant to said target gas species.

30. The gas-sensing assembly of claim 28, wherein the support structure comprises polyimide or aluminum.

31. The gas-sensing assembly of claim 28, wherein said one or more gas-sensing filaments of the elongated gas sensor element contain nickel or nickel alloy.

32. The gas-sensing assembly of claim 31, wherein said one or more gas-sensing filaments of the elongated gas sensor element are electrochemically thinned after fabrication of said assembly to achieve an average diameter of not more than 50 microns.

33. The gas-sensing assembly of claim 31, wherein said one or more gas-sensing filaments of the elongated gas sensor element are characterized by an average diameter of not more than 25 microns.

34. The gas-sensing assembly of claim 31, wherein said one or more gas-sensing filaments of the elongated gas sensor element are characterized by an average diameter of not more than 10 microns.

35. The gas-sensing assembly of claim 31, wherein said one or more gas-sensing filaments of the elongated gas sensor element are characterized by an average diameter in a range of from about 0.1 micron to about 5 microns.

36. A method for monitoring a fluid locus for the presence of a target gas species therein, said method comprising:
    exposing fluid at said fluid locus to a gas-sensing assembly as in claim 26;
    monitoring at least one property of the elongated gas sensor element of such gas-sensing assembly; and
    responsively generating an output signal when the elongated gas sensor element exhibits a change in the at least one property thereof, indicating the presence of the target gas species in the fluid locus, or a change in concentration of the target gas species in the fluid locus.

37. The method of claim 36, wherein said at least one property of the elongated gas sensor element being monitored is the electrical resistance thereof.

38. A gas-sensing assembly arranged in sensing relationship to a process chamber that is susceptible to presence of one or more target fluoro gas species, said gas-sensing assembly comprising:
    a nickel-containing gas sensor element mounted on a surface of a support structure, having a longitudinal axis that is oriented perpendicular to or substantially perpendicular to the mounting surface of the support structure, and being interactive with the target fluoro gas species;
    a detector, coupled to the sensor element, adapted to detect a change in at least one property of said gas sensor element upon contact of the gas sensor element with the target fluoro gas species; and
    a signal generator adapted to generate an output signal indicative of any of the presence and the concentration of said target fluoro gas species.

39. The elongated gas sensor element of claim 1, wherein the signal is indicative of presence of the at least one gas species.

40. The elongated gas sensor element of claim 1, wherein the signal is indicative of concentration of the at least one gas species.

41. The elongated gas sensor element of claim 1, wherein the filament is fluoro-reactive.

* * * * *